United States Patent [19]

Nikolaides et al.

[11] Patent Number: 5,648,516

[45] Date of Patent: Jul. 15, 1997

[54] FUSED CYCLOALKYLIMIDAZOPYRIDINES

[75] Inventors: Nick Nikolaides; John F. Gerster, both of Woodbury, Minn.

[73] Assignee: Minnesota Mining and Manufacturing Company, St Paul, Minn.

[21] Appl. No.: 471,442

[22] Filed: May 31, 1995

Related U.S. Application Data

[62] Division of Ser. No. 277,959, Jul. 20, 1994, Pat. No. 5,444,065.

[51] Int. Cl.$^6$ .................................................. C07C 229/30
[52] U.S. Cl. ............................................................. 560/125
[58] Field of Search ............................................. 560/125

[56] References Cited

U.S. PATENT DOCUMENTS

| | | | |
|---|---|---|---|
| 3,899,508 | 8/1975 | Wikel | 260/310 R |
| 4,689,338 | 8/1987 | Gerster | 514/293 |
| 4,698,348 | 10/1987 | Gerster | 514/293 |
| 4,929,624 | 5/1990 | Gerster et al. | 514/293 |
| 4,988,815 | 1/1991 | Andre et al. | 546/159 |
| 5,037,986 | 8/1991 | Gerster | 546/82 |
| 5,175,296 | 12/1992 | Gerster | 546/82 |
| 5,266,575 | 11/1993 | Gerster et al. | 514/293 |
| 5,268,376 | 12/1993 | Gerster | 514/293 |
| 5,346,905 | 9/1994 | Gerster | 514/293 |
| 5,352,784 | 10/1994 | Nikolaides et al. | 594/126 |

FOREIGN PATENT DOCUMENTS

| | | |
|---|---|---|
| 0385630 A2 | 9/1990 | European Pat. Off. . |
| 0394026 A2 | 10/1990 | European Pat. Off. . |
| 0510260 A2 | 10/1992 | European Pat. Off. . |
| US91/06682 | 4/1992 | WIPO . |
| US92/01305 | 9/1992 | WIPO . |
| US92/07226 | 3/1993 | WIPO . |

OTHER PUBLICATIONS

Tomioka K, Audo K, Takemasa Y, Kozak. J. Am Chem. Soc. (1984), 106 (9), 2718–9.
J. Med. Chem., 1968, 11, 87 (Jain et al.).
J. Org. Chem., 1978, 43, 1460 (Kloek et al.).
Helv. Chem. Acta. 1945, 28, 1684 (Prelog et al.).
J. Med. Chem. 1975, 18, 726 (Buckle et al.).
Methods in Enzymology, 1981, 78, 262–284 (Stringfellow).

*Primary Examiner*—C. Warren Ivy
*Assistant Examiner*—Evelyn Huang
*Attorney, Agent, or Firm*—Gary L. Griswold; Walter N. Kirn; Ted K. Ringsred

[57] ABSTRACT

6,7-propylene-, butylene-, or pentylene-bridged imidazopyridin-4-amines that induce interferon ($\alpha$) biosynthesis in human cells, their pharmaceutical compositions containing such compounds and methods of inducing interferon ($\alpha$) biosynthesis and treating viral infections involving the use of such compounds are disclosed.

1 Claim, No Drawings

FUSED CYCLOALKYLIMIDAZOPYRIDINES

This is a division of application Ser. No. 08/277,959 filed Jul. 20, 1994, now U.S. Pat. No. 5,444,065.

BACKGROUND OF THE INVENTION

1. Field of the Invention

This invention relates to imidazopyridine compounds and to intermediates in their preparation. In another aspect this invention relates to immunomodulator compounds and to antiviral compounds.

2. Description of the Related Art

Certain 1H-imidazo[4,5-c]quinolin-4-amines and methods for their preparation are known and disclosed, e.g., in U.S. Pat. Nos. 4,689,338, 5,037,985, and 5,175,296, EP-A 90.301766.3, PCT/US91/06682, PCT/US92/01305, and PCT/US92/07226 (Gerster), and U.S. Pat. No. 4,988,815 (Andre et al). Such compounds are said to have antiviral activity and certain of them are said to induce the biosynthesis of cytokines such as interferon.

Further compounds having antiviral or immunomodulator activity may advance the fields of antiviral therapy and immunomodulator therapy.

SUMMARY OF THE INVENTION

This invention provides 6,7-propylene-, butylene-, or pentylene-bridged imidazopyridin-4-amines that are active as immunomodulators.

This invention also provides compounds of Formula V:

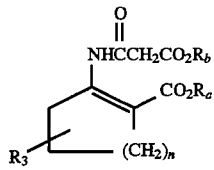

wherein n is 1, 2, or 3, $R_3$ is selected from the group consisting of hydrogen, fluoro, chloro, straight chain or branched chain alkyl containing one to about four carbon atoms, and straight chain or branched chain fluoro- or chloroalkyl containing one to about four carbon atoms and at least one fluorine or chlorine atom, $R_a$ is a group that renders the associated ester group susceptible of nucleophilic attack by an anion derived from an active methylene compound, and $R_b$ is a group that renders the associated ester group susceptible of hydrolysis.

This invention also provides compounds of Formula IX:

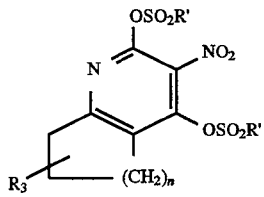

wherein n and $R_3$ are as defined above and R' is alkyl (e.g., lower alkyl such as methyl), perfluoroalkyl (e.g., perfluoro(lower)alkyl such as trifluoromethyl), phenyl, phenylalkyl (e.g., phenyl(lower)alkyl such as 4-methylphenyl), alkylphenyl (e.g., (lower)alkylphenyl such as methylphenyl), or halophenyl (e.g., 4-bromophenyl).

This invention also provides compounds of Formula X:

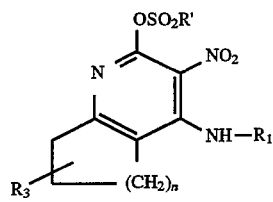

wherein n, $R_3$, and R' are as defined above and $R_1$ is selected from the group consisting of hydrogen; cyclic alkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; fluoro- or chloroalkyl containing from one to about 10 carbon atoms and one or more fluorine or chlorine atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;
and

wherein $R_y$ is hydrogen or a carbon-carbon bond, with the proviso that when $R_y$ is hydrogen $R_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $T_y$ is a carbon-carbon bond $R_y$ and $R_x$ together form a tetrahydrofuranyl group optionally substituted with one or more substituents independently selected from the group consisting of hydroxy and hydroxyalkyl of one to about four carbon atoms.

This invention also provides compounds of Formulas XI and XII:

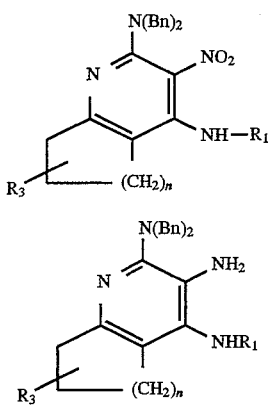

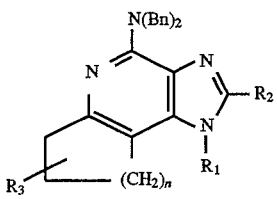

wherein n, $R_1$, and $R_3$ are as defined above and Bn represents a hydrogenolyzable amino substituent.

This invention also provides compounds of Formula XIII:

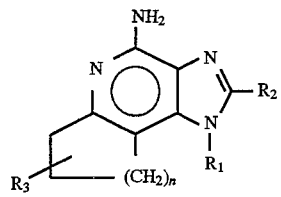

wherein n, $R_1$, $R_3$, and Bn are as defined above and $R_2$ is selected from the group consisting of hydrogen, straight chain or branched chain alkyl containing one to about eight carbon atoms, straight chain or branched chain hydroxyalkyl containing one to about six carbon atoms, benzyl, (phenyl) ethyl and phenyl, the benzyl, (phenyl)ethyl or phenyl substituent being optionally substituted on the benzene ring by a moiety selected from the group consisting of methyl, methoxy, and halogen; and —$C(R_s)(R_t)(X)$ wherein $R_S$ and $R_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms, and morpholinoalkyl wherein the alkyl moiety contains one to about four carbon atoms.

This invention also provides a pharmaceutical composition comprising a therapeutically effective amount of a 6,7-propylene-, butylene-, or pentylene-bridged imidazopyridin-4-amine and a pharmaceutically acceptable vehicle.

This invention also provides a method of inducing interferon biosynthesis in an animal, comprising the step of administering to said animal a 6,7-propylene-, butylene-, or pentylene-bridged imidazopyridin-4-amine in an amount effective to induce said interferon biosynthesis.

DETAILED DESCRIPTION OF THE INVENTION

The immunomodulator 6,7-propylene-, butylene-, or pentylene-bridged imidazopyridin-4-amines of this invention are compounds of the general Formula I:

In Formula I, n is 1, 2, or 3. $R_1$, $R_2$, and $R_3$ are independently selected and can be any substituent that does not destroy the immunomodulator activity of the compound (as that activity is determined by the test method set forth in detail in the Examples below in connection with interferon ($\alpha$) induction in human cells). Suitable substituents can be selected by those skilled in the art with due consideration of factors such as drug solubility, lipophilicity/hydrophilicity, ionization, and other factors that affect drug transfer across membranes. Exemplary $R_1$ substituents include hydrogen; cyclic alkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; fluoro- or chloroalkyl containing from one to about ten carbon atoms and one or more fluorine or chlorine atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms; and —$CHR_xR_y$ wherein
$R_y$ is hydrogen or a carbon-carbon bond, with the proviso that when $R_y$ is hydrogen $R_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to about four carbon atoms.

Preferred $R_1$ substituents include straight chain or branched chain alkyl containing one to about ten carbon atoms, substituted straight chain or branched chain alkyl containing one to about ten carbon atoms wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain hydroxyalkyl containing one to about six carbon atoms, with the proviso that any alkyl, substituted alkyl, or hydroxyalkyl group does not contain a fully carbon substituted carbon atom bonded directly to the nitrogen atom; phenyl; and phenylethyl.

$R_1$ is most preferably alkyl, (phenyl)ethyl, or hydroxyalkyl as defined above. When $R_1$ is alkyl as defined above, preferred $R_1$ substituents include 2-methylpropyl, 1-methylpropyl, n-butyl, and cyclohexylmethyl. When $R_1$ is hydroxyalkyl as defined above preferred $R_1$ substituents include 2-hydroxy-2-methylpropyl and 3-hydroxypropyl.

Exemplary $R_2$ substituents include hydrogen, straight chain or branched chain alkyl containing one to about eight carbon atoms, straight chain or branched chain hydroxyalkyl containing one to about six carbon atoms, benzyl, (phenyl) ethyl and phenyl, the benzyl, (phenyl)ethyl or phenyl substituent being optionally substituted on the benzene ring by a moiety selected from the group consisting of methyl, methoxy, and halogen; and —C($R_s$)($R_r$)(X) wherein $R_S$ and $R_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms, and morpholinoalkyl wherein the alkyl moiety contains one to about four carbon atoms.

$R_2$ is most preferably hydrogen, alkyl, hydroxyalkyl, morpholinoalkyl, or alkoxyalkyl as defined above, or benzyl. When $R_2$ is alkyl it is preferably methyl, ethyl, or 1-methylethyl, or 2-methylpropyl. When $R_2$ is hydroxyalkyl it is preferably hydroxymethyl. When $R_2$ is morpholinoalkyl it is preferably morpholinomethyl.

When $R_2$ is alkoxyalkyl, it is preferably methoxymethyl or ethoxymethyl.

Exemplary $R_3$ substituents include hydrogen, fluoro, chloro, straight chain or branched chain alkyl containing one to about four carbon atoms, and straight chain or branched chain fluoro- or chloroalkyl containing one to about four carbon atoms and at least one fluorine or chlorine atom. $R_3$ is preferably hydrogen.

Preferred compounds of the invention include:
6,7,8,9-tetrahydro-1,2-di(2-methylpropyl)-1H-imidazo[4,5-c]quinolin-4-amine,
6,7,8,9-tetrahydro-2-methyl-1-(2-methylpropyl)-1H-imidazo[4,5-c]quinolin-4-amine,
7,8-dihydro-2-methyl-1-(2-methylpropyl)-1H,6H-imidazo[4,5-d]pyrindin-4-amine,
4-amino-α,α-dimethyl-1,6,7,8,9,10-hexahydrocyclohepta[b]imidazo[4,5-d]pyridine-1-ethanol,
1,6,7,8,9,10-hexahydro-1-(2-methylpropyl)cyclohepta[b]imidazo[4,5-d]pyridin-4-amine,
4-amino-α,α-dimethyl-6,7,8,9-tetrahydro-1H-imidazo[4,5-c]quinolin-1-ethanol,
6,7,8,9-tetrahydro-2-methoxymethyl-1-(2-methylpropyl) 1H-imidazo[4,5-c]quinolin-4-amine,
6,7,8,9-tetrahydro-1-(2-methylpropyl)-1H-imidazo[4,5-c]quinolin-4-amine,
4-amino-6,7,8,9-tetrahydro-1H-imidazo[4,5-c]quinoline-1-propanol,
6,7,8,9-tetrahydro-1-phenyl-1H-imidazo[4,5-c]quinolin-4-amine,
6,7,8,9-tetrahydro-1-(2-phenylethyl)-1H-imidazo[4,5-c]quinolin-4-amine,
1-cyclohexylmethyl-6,7,8,9-tetrahydro-1H-imidazo[4,5-c]quinolin-4-amine,
6,7,8,9-tetrahydro-1-(1-methylpropyl)-1H-imidazo[4,5-c]quinolin-4-amine,
1-butyl-6,7,8,9-tetrahydro-1H-imidazo[4,5-c]quinolin-4-amine,
7,8-dihydro-1-(2-methylpropyl)-1H,6H-imidazo[4,5-d]pyrindin-4-amine,
1,6,7,8,9,10-hexahydro-2-methyl-1-(2-methylpropyl)cyclohepta[b]imidazo[4,5-d]pyridin-4-amine,
4-amino-1,6,7,8,9,10-hexahydro-α,α,2-trimethylcyclohepta[b]imidazo[4,5-d]pyridine-1-ethanol,
4-amino-6,7,8,9-tetrahydro-α,α,2-trimethyl-1H-imidazo[4,5-c]quinolin-1-ethanol,
2-ethyl-6,7,8,9-tetrahydro-1-(2-methylpropyl)-1H-imidazo[4,5-c]quinolin-4-amine,
6,7,8,9-tetrahydro-1-(2-methylpropyl)-2-(1-methylpropyl)-1H-imidazo[4,5-c]quinolin-4-amine,
4-amino-α,α-dimethyl-2-ethoxymethyl-6,7,8,9-tetrahydro-1H-imidazo[4,5-c]quinolin-1-ethanol,
6,7,8,9-tetrahydro-1-(2-methylpropyl)-2-phenylmethyl-1H-imidazo[4,5-c]quinolin-4-amine,
4-amino-6,7,8,9-tetrahydro-1-(2-methylpropyl)-1H-imidazo[4,5-c]quinolin-2-methanol,
6,7,8,9-tetrahydro-1-(2-methylpropyl)-2-morpholinomethyl-1H-imidazo[4,5-c]quinolin-4-amine,
6,7,8,9-tetrahydro-1-phenylmethyl-1H-imidazo[4,5-c]quinolin-amine, and
6,7,8,9-tetrahydro-1H-imidazo[4,5-c]quinolin-4-amine.

Compounds of the invention can be prepared according to Reaction Scheme I, wherein n, $R_1$, $R_2$, and $R_3$ are as defined above. Reaction Scheme I is particularly amenable to the preparation of compounds wherein $R_1$, $R_2$, and $R_3$ are selected from the preferred substituents enumerated above.

Reaction Scheme

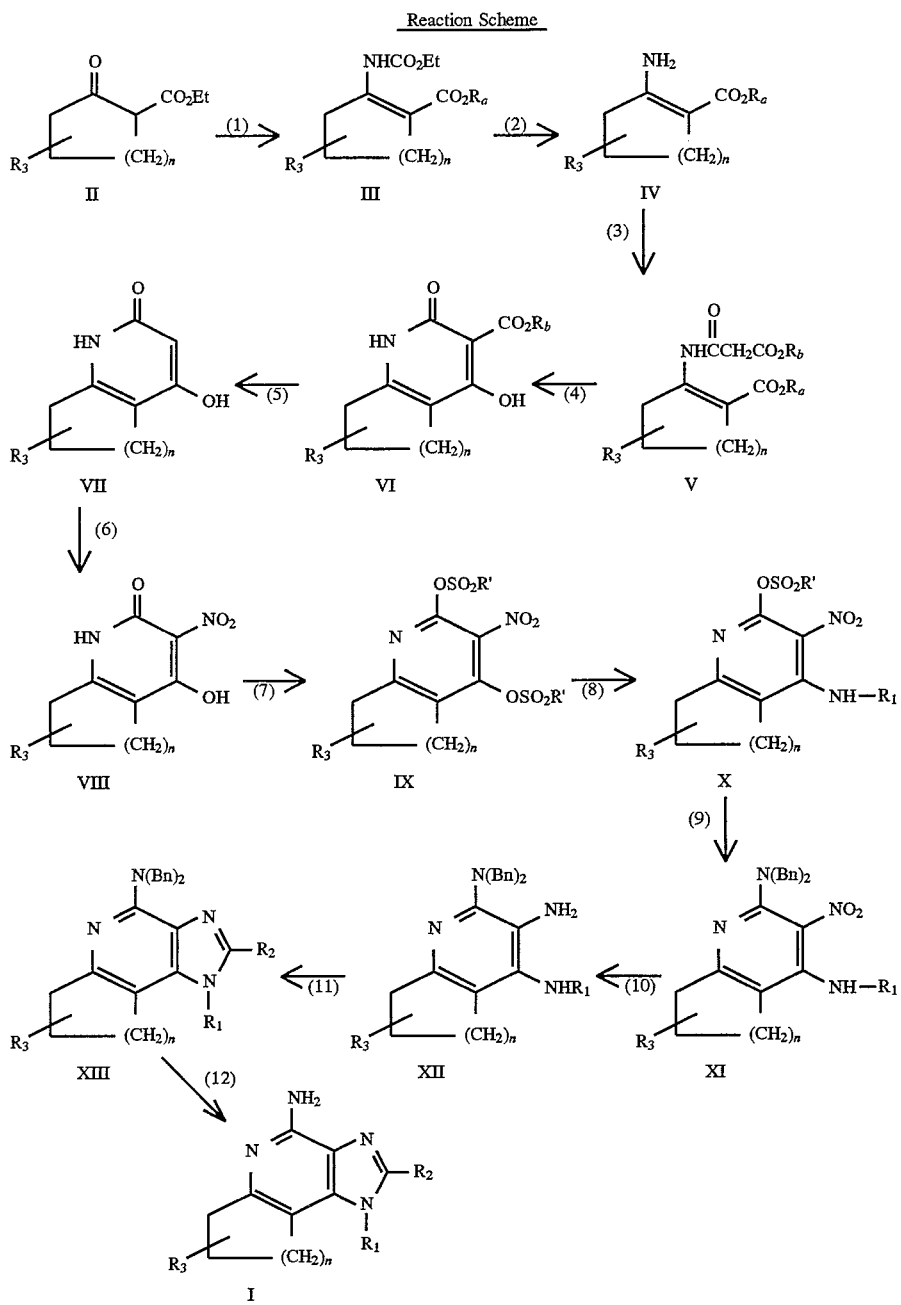

Cyclic β-ketoesters of Formula II in the Reaction Scheme can be prepared using conventional reactions such as the Dieckman condensation. In step (1) of Reaction Scheme I, a compound of Formula II is reacted with urethane or another appropriate carboxylamine ester with heating in the presence of an acid catalyst (e.g., p-toluenesulfonic acid), preferably in a solvent (e.g., benzene, toluene) that allows azeotropic removal of water to afford a compound of Formula III. Alkoxide-catalyzed alcoholysis in step (2) affords a compound of Formula IV, wherein $R_a$ is a group, e.g., an alkyl group, that renders the ester group susceptible of nucleophilic attack by an anion derived from an active methylene compound. Certain compounds of Formula IV are known and disclosed, e.g., in *J. Org. Chem.* 1978, 43, 1460 (Kloek, et al.) and *Helv. Chem. Acta.* 1945, 28, 1684 (Prelog, et al.).

In step (3) the amino group of the compound of Formula IV is acylated by reacting with an alkyl malonyl chloride in the presence of a base such as triethylamine and in a suitable solvent such as methylene chloride to provide a compound of Formula V wherein $R_b$ is a group, e.g., alkyl, that renders the ester group susceptible of hydrolysis. Certain compounds of Formula V are known and disclosed, e.g., in *J. Med. Chem.* 1975, 18, 726 (Buckle et al.).

In step (4) the compound of Formula V is cyclized by reacting in an appropriate solvent in the presence of a base (e.g., sodium hydride) capable of removing a malonyl methylene proton. If necessary the reaction can be heated. Certain compounds of Formula VI are known and disclosed, e.g., in *J. Med. Chem.* 1975, 18, 726 (Buckle et al.).

In step (5) a compound of Formula VI is hydrolyzed and decarboxylated, e.g., by heating in the presence of an acid catalyst (such as HCl) or a base catalyst (such as hydroxide) in order to afford a compound of Formula VII. Certain compounds of Formula VII are known and disclosed, e.g., in *J. Med. Chem.* 1975, 18, 726 (Buckle et al.) and in *Helv. Chem. Acta.* 1945, 28, 1684 (Prelog et al.).

A compound of Formula VII is nitrated in step (6) under conventional nitration conditions, such as by heating.(e.g., to 100° C.) in the presence of nitric acid, preferably in a solvent such as acetic acid. The product is a compound of Formula VIII, some of which are known and disclosed, e.g., in *J. Med. Chem.* 1975, 18, 726 (Buckle et al.).

In step (7) a 5,6-propylene-, butylene-, or pentylene-bridged-3-nitropyridine-2,4-disulfonate of Formula IX is provided by reacting a compound of Formula VIII with a sulfonyl halide or preferably a sulfonic anhydride. Suitable sulfonyl halides include alkylsulfonyl halides such as methanesulfonyl chloride and trifluoromethanesulfonyl chloride, and arylsulfonyl halides such as benzenesulfonyl chloride, p-bromobenzenesulfonyl chloride, and p-toluenesulfonyl chloride. Suitable sulfonic anhydrides include those corresponding to the above-mentioned sulfonyl halides. A particularly preferred sulfonic anhydride is trifluoromethanesulfonic anhydride. Sulfonic anhydrides are preferred in view of the fact that the sulfonate anion generated as a byproduct of the reaction is a relatively poor nucleophile and as such does not give rise to undesired side products such as those in which the nitro group has been displaced.

Reaction conditions preferably involve first combining a compound of Formula VIII with a base, preferably an excess of a tertiary amine base (e.g., a trialkylamine base such as triethylamine) and preferably in an appropriate solvent such as dichloromethane and then adding the sulfonyl halide or the sulfonic anhydride. The addition is preferably carried out in a controlled fashion (e.g., dropwise) and at a reduced temperature (e.g., at about 0° C.). The product can be isolated by conventional methods or it can be carried on without isolation as described below in connection with step (8).

Step (8) of the Reaction Scheme provides the product 5,6-propylene-, butylene-, or pentylene-bridged 3-nitro-4-(substituted)aminopyridine-2-sulfonates from the compound of Formula VIII. Despite the presence of two sulfonate groups that could in principle be displaced, the reaction results in selective amination at the 4-position. The compound of Formula IX is reacted with an amine, preferably in the presence of an excess of a tertiary amine base in a solvent such as dichloromethane. Suitable amines include primary amines affording 4-substituted amino compounds of Formula X herein the amino substituent is represented by $R_1$. Preferred amines include those amines comprising the groups set forth above in connection with preferred $R_1$ substituents.

The reaction can be carried out by adding the tertiary amine base to the reaction mixture resulting from step (7), cooling to a reduced temperature (e.g., 0° C.), and adding the amine in a controlled fashion (e.g., dropwise). The reaction can also be carried out by adding the amine to a solution of the compound of Formula IX and a tertiary amine base in a solvent such as dichloromethane. As the sulfonate is a relatively facile leaving group the reaction can be run at relatively low temperatures, e.g., about 0° C., and in relatively non-polar solvents (e.g., toluene) in order to decrease the amount of undesired 2-aminated and 2,4-diaminated side products. It is sometimes necessary or desirable to heat the reaction mixture after the addition in order to complete the reaction. The product can be isolated from the reaction mixture by conventional methods.

In step (9) the compound of Formula X is reacted with a hydrogenolyzable amine to afford a compound of Formula XI. The term "hydrogenolyzable amine" as used herein refers to any amine that is nucleophilic enough to displace the sulfonate group in step (9) and wherein the substituent or substituents can be removed by hydrogenolysis. Such amines are known to those skilled in the art to include arylmethyl amines and di(arylmethyl) amines, i.e., those amines wherein the substituent or substituents are identical or different from one another and with respect to each substituent the amino nitrogen is one carbon removed from an aromatic ring. The term "hydrogenolyzable amino substituent" as used herein refers to the substituent that obtains upon the use of a hydrogenolyzable amine in the reaction of step (9), i.e., a hydrogenolyzable amine absent one hydrogen atom. Primary hydrogenolyzable amines are less preferred, as their use provides an alternative site for cyclization in step (11) described below. Secondary hydrogenolyzable amines are preferred. Suitable secondary hydrogenolyzable amines include dibenzylamine (i.e., di(phenylmethyl)amine) and substituted derivatives thereof such as di[4-methyl(phenylmethyl)]amine, di(2-furanylmethyl)amine, and the like. The Reaction Scheme specifically illustrates the process involving dibenzylamine. However, the process of the invention can be carried out with any suitable hydrogenolyzable amine.

The reaction of step (9) can be carried out by placing the starting material and the hydrogenolyzable amine in an inert solvent such as benzene, toluene, or xylene, and heating at a temperature and for a time sufficient to cause displacement of the sulfonate group by the hydrogenolyzable amine, such temperature and time being readily selected by those skilled in the art. The product can be isolated from the reaction mixture by conventional methods.

In step (10) the nitro group of a compound of Formula XI is reduced to an amino group. Methods for such a reduction are well known to those skilled in the art. A preferred method involves in situ generation of $Ni_2B$ from sodium borohydride and $NiCl_2$ in the presence of methanol. The compound of Formula XI is added to the reducing agent solution to effect reduction of the nitro group. The product can then be isolated by conventional methods.

In step (11) a compound of Formula XII is reacted with a carboxylic acid or an equivalent thereof to afford the cyclized compound of Formula XIII. Suitable equivalents to a carboxylic acid include acid halides, orthoesters, and orthoformates, orthoesters, acid halides, and carboxylic acids other than formic acid giving rise to 2-substituted products wherein the 2-substituent is represented by $R_2$. The reaction can be run in the absence of solvent or preferably in an inert solvent such as xylene or toluene in the presence of a carboxylic acid or equivalent with sufficient heating (e.g., at about 80°–150° C. depending on the solvent if any) to drive off any alcohol or water formed as a side product of the reaction.

In step (12) the cyclized compound of Formula XIII is hydrogenolyzed to afford the 4-amino compound. Conventional well known catalytic hydrogenation conditions are suitable. Preferred conditions involve heating in formic acid in the presence of $Pd(OH)_2/C$.

Certain compounds of the invention cannot be prepared readily according to Reaction Scheme I due to incompatibility of reagents with certain of the functional groups recited in connection with $R_1$, $R_2$, and $R_3$. Such compounds, however, can be prepared by those skilled in the art using well known methods of functional group protection or manipulation, by using compounds of Formula VII as substrates in the synthetic methods disclosed in U.S. Pat. Nos. 4,988,815 (Andre), or by adaptations of the synthetic methods disclosed in U.S. Pat. Nos. 4,689,338, 5,037,985, and 5,175,296, EP-A 90.301766.3, PCT/US91/06682, PCT/US92/01305, and PCT/US92/07226 (Gerster), the relevant disclosures of each of these being incorporated herein by reference.

The product compound of Formula I can be isolated by the conventional means disclosed in U.S. Pat. No. 4,689,338 (Gerster), such as, for example, removal of the solvent and recrystallization from an appropriate solvent (e.g., N,N-dimethylformamide) or solvent mixture, by dissolution in an appropriate solvent (such as methanol) and re-precipitation by addition of a second solvent in which the compound is insoluble, or by column chromatography.

A compound of Formula I can be used as an immunomodulating agent itself or it can be used in the form of a pharmaceutically acceptable acid-addition salt such as a hydrochloride, dihydrogen sulfate, trihydrogen phosphate, hydrogen nitrate, methanesulfonate or a salt of another pharmaceutically acceptable acid. A pharmaceutically acceptable acid-addition salt of a compound of Formula I can be prepared, generally by reaction of the compound with an equimolar amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration in a pharmaceutically acceptable vehicle, such as water or polyethylene glycol, along with suitable adjuvants, excipients, and the like. Particular formulations can be readily selected by those skilled in the art. Suitable formulations for topical application include creams, ointments and like formulations known to those skilled in the art (e.g., formulations analogous to those disclosed in commonly assigned copending application 07/845,323, incorporated herein by reference). Parenteral formulations are also suitable (e.g., formulations analogous to those disclosed in EP-A-90.304812.0, incorporated herein by reference).

A pharmaceutical composition of the invention comprises a therapeutically effective amount of a bridged imidazopyridin-4-amine. The amount that constitutes a therapeutically effective amount will depend on the particular compound, the particular formulation, the route of administration, and the intended therapeutic effect. Those skilled in the art can determine a therapeutically effective amount with due consideration of such factors.

A number of compounds of Formula I were tested and found to induce biosynthesis of interferon in human cells. The test methods and results are set forth below. As a result of this immunomodulating activity the compounds exhibit antiviral and antitumor activity. For example, a compound of Formula I can be used as an agent to control infections in mammals caused by Type II Herpes simplex virus. Compounds of Formula I can also be used to treat a herpes infection by oral, topical, or intraperitoneal administration. The results below suggest that at least certain compounds of the invention might be useful in treating other diseases such as warts, Hepatitis B and other viral infections, cancer such as basal cell carcinoma, and other neoplastic diseases.

In the following Examples, all reactions were run with stirring under an atmosphere of dry nitrogen unless otherwise indicated. The structures were confirmed by nuclear magnetic spectroscopy. The particular materials and amounts thereof recited in the Examples, as well as other conditions and details, should not be construed to unduly limit the invention.

EXAMPLE 1

6,7-Dihydro-4-[(2-methylpropyl)amino]-3-nitro-5H-pyrindin-2-yl Trifluoromethanesulfonate Part A A solution containing ethyl 2-oxocyclopentanecarboxylate (90 g, 0.63 moles), urethane (63.1 g, 0.70 mole) and p-toluenesulfonic acid (1 g) in benzene (100 mL) was refluxed for 15 hours in a Soxhlet extraction apparatus with sodium sulfate in the thimble. The reaction mixture was washed with water (3×100 mL), dried over magnesium sulfate then evaporated under vacuum. The resulting residue was recrystallized from methanol:water (9:1) to provide 92.1 g of ethyl 2-[(ethoxycarbonyl)amino]-1-cyclopentene-1-carboxylate as a white solid, m.p. 49°–51° C.

Part B

A solution containing ethyl 2-[(ethoxycarbonyl)-amino]-1-cyclopentene-1-carboxylate (72 g, 0.32 moles) and 25 wt % sodium methoxide in methanol (91.5 mL, 0.40 moles) was refluxed for about 18 hours. Methanol (200 mL) was added during the course of the reaction. The reaction mixture was allowed to cool to ambient temperature then diluted with water and extracted with diethyl ether (5×100 mL). The ether extracts were combined, treated with activated charcoal, dried over sodium sulfate then evaporated to provide 43.8 g of ethyl 2-amino-1-cyclopentene-1-carboxylate as an ivory solid, m.p. 90°–92° C.

Part C

Ethyl 2-amino-1-cyclopentene-1-carboxylate (43.8 g, 0.28 moles) was combined with triethyl amine (42.9 mL, 0.31 moles) and methylene chloride (850 mL) and cooled to 0° C. Methyl malonyl chloride (33.4 mL, 0.31 mole) was added dropwise to the reaction mixture. After the addition the reaction was stirred for about 1 hr at 0° C. The reaction mixture was quenched with water (500 mL). The layers were separated. The aqueous layer was extracted with methylene chloride (4 ×100 mL). The organic layers were combined, dried over magnesium sulfate and evaporated under vacuum to provide 56.2 g of an oil. The oil was purified by silica gel chromatography eluting with hexane:ethyl acetate (70:30) to provide 46 g of methyl 3-oxo-3-[(2-ethoxycarbonylcyclopenten-1-yl)amino]propanoate as a clear oil.

Part D

A solution containing methyl 3-oxo-3-[(2-ethoxycarbonylcyclopenten-1-yl)amino]propanoate (3.5 g, 13.8 mmole) in tetrahydrofuran (10 mL) was added to a suspension of sodium hydride (0.83 g, 27.6 mmole as an 80% dispersion in mineral oil) in tetrahydrofuran (50 mL). The reaction mixture was refluxed for 4 hours then concentrated under vacuum to remove the tetrahydrofuran. The residue was diluted with methanol (5 mL) then with water (100 mL) then acidified with 2N hydrochloric acid. The resulting precipitate was isolated by filtration and dried to provide 1.46 g of methyl 2,5,6,7-tetrahydro-4-hydroxy-2-oxo-1H-pyrindine-3-carboxylate as a white solid, m.p. 131°–133° C.

Part E

Methyl 2,5,6,7-tetrahydro-4-hydroxy-2-oxo-1H-pyrindine-3-carboxylate (10.1 g, 48 mmole) was combined with 3N hydrochloric acid and heated at reflux for 48 hours. The reaction mixture was cooled to 0° C. and the pH was adjusted to pH 4 with 2N sodium hydroxide. The resulting precipitate was isolated by filtration and dried to provide 6.5 g of 1,5,6,7-tetrahydro-4-hydroxy-2H-pyrindin-2-one as a beige solid, m.p. >310° C.

Part F

Nitric acid (10.55 mL) was added to a suspension of 2,5,6,7-tetrahydro-4-hydroxy-2H-pyrindin-2-one (5.8 g, 38 mmole) in glacial acetic acid (42.2 mL). The reaction mixture was heated briefly on a steam bath until a vigorous reaction ensued. The reaction mixture was cooled rapidly by placing the reaction flask on ice then adding ice (about 170 g) to the reaction mixture. The resulting precipitate was isolated by filtration, washed with water then dried to provide 4.2 g of a yellow solid, m.p. 232°–234° C. This material was combined with that obtained from additional runs of the reaction and recrystallized from ethanol to provide 11.5 g of 1,5,6,7-tetrahydro-4-hydroxy-3-nitro-2H-pyrindin-2-one as a yellow crystalline solid, m.p. 239°–241° C.

Part G

Triethylamine (1.4 mL) was added to a cooled (0° C.) suspension of 1,5,6,7-tetrahydro-4-hydroxy-3-nitro-2H-pyrindin-2-one (1.0 g, 5 mmole) in methylene chloride (40 mL). The resulting solution was stirred at 0° C. for 15 minutes. Trifluoromethanesulfonic anhydride (1.7 mL, 10 mmole) was slowly added using a syringe. The reaction mixture was then stirred at 0° C. for 30 minutes. Isobutylamine (1.5 mL, 15 mmole) was added and the reaction was stirred at 0° C. for 20 minutes then allowed to sit at room temperature for 30 minutes. The reaction mixture was diluted with water then extracted with methylene chloride (3×80 mL). The extracts were combined, dried over magnesium sulfate then evaporated under vacuum without heating to provide a brown oil. The oil was purified by silica gel chromatography eluting with hexane:ethyl acetate 80:20 to provide 1.6 g of 6,7-dihydro-[4-(2-methylpropyl)amino]-3-nitro-5H-pyrindin-2-yl trifluoromethanesulfonate as an oil which solidified after being refrigerated. Analysis: Calculated for $C_{13}H_{16}F_3N_3O_5S$: %C, 40.73; %H, 4.21; %N, 10.96; Found: %C, 40.75; %H, 4.23; %N, 10.90.

EXAMPLE 2

5,6,7,8,9-Pentahydro-[4-(2-methylpropyl)amino-3-nitrocyclohepta[b]pyridin-2-yl] Trifluoromethanesulfonate Part A Using the method of Example 1 Part A, methyl 2-oxocycloheptanecarboxylate (50.5 g, 0.30 mole) was reacted with urethane to provide 59 g of methyl 2-[(ethoxycarbonyl)amino]-1-cycloheptene-1-carboxylate as an oil.

Part B

Using the method of Example 1 Part B, methyl 2-[(ethoxycarbonyl)amino]-1-cycloheptene-1-carboxylate (59 g, 0.24 mole) was reacted with sodium methoxide to provide 30 g of methyl 2-amino-1-cycloheptene-1-carboxylate as an off white solid.

Part C

Using the method of Example 1 Part C, methyl 2-amino-1-cycloheptene-1-carboxylate (29.7 g, 0.17 mole) was reacted with methyl malonyl chloride to provide 41 g of methyl 3-oxo-3-[(2-ethoxycarbonylcyclohepten-1-yl)amino]propanoate as an oil.

Part D

Using the method of Example 1 Part D, methyl 3-oxo-3-[(2-ethoxycarbonylcyclohepten-1-yl)amino]propanoate (41 g, 0.15 mole) was cyclized to provide 30 g of methyl 2,5,6,7,8,9-hexahydro-4-hydroxy-2-oxo-1H-cyclohepta[b]pyridine-3-carboxylate as a beige solid, m.p. >255° C.

Part E

Using the method of Example 1 Part E, methyl 2,5,6,7,8,9-hexahydro-4-hydroxy-2-oxo-1H-cyclohepta[b]pyridine-3-carboxylate (29.9 g, 0.126 moles) was hydrolyzed and decarboxylated to provide 22.7 g of 1,5,6,7,8,9-hexahydro-4-hydroxy-2H-cyclohepta[b]pyridin-2-one as an off white solid, m.p. >270° C.

Part F

Using the method of Example 1 Part F, 1,5,6,7,8,9-hexahydro-4-hydroxy-2H-cyclohepta[b]pyridin-2-one (22.7 g, 0.126 mole) was nitrated to provide 21 g of 1,5,6,7,8,9-hexahydro-4-hydroxy-3-nitro-2H-cyclohepta[b]pyridin-2-one as a yellow solid, m.p. >264° C.

Part G

Using the method of Example 1 Part G, 1,5,6,7,8,9-hexahydro-4-hydroxy-3-nitro-2H-cyclohepta[b]pyridin-2-one (4.7 g, 21 mmole) was reacted first with trifluoromethanesulfonic anhydride then with isobutylamine to provide 5.4 g of 5,6,7,8,9-pentahydro-[4-(2-methylpropyl)amino-3-nitrocyclohepta[b]pyridin-2-yl] trifluoromethanesulfonate.

EXAMPLE 3

5,6,7,8,9-Pentahydro-[4-(2-hydroxy-2-methylpropyl)amino-3-nitrocyclohepta[b]pyridin-2-yl] Trifluoromethanesulfonate Using the method of Example 1 Part G, 1,5,6,7,8,9-hexahydro-4-hydroxy-3-nitro-2H-cyclohepta[p]pyridin-2-one (1.0 g, 4.4. mmole) was first reacted with trifluoromethanesulfonic anhydride then with 2-amino-α,α-dimethylethanol to provide 1.5 g of the desired product as a yellow oil.

EXAMPLE 4

5,6,7,8-Tetrahydro-[4-(2-methylpropyl)amino-3-nitroquinolin-2-yl] Trifluoromethanesulfonate Part A Using the method of Example 1 Part A, ethyl 2-oxocyclohexanecarboxylate (201 g, 1.18 mole) was reacted with urethane to provide 135 g of ethyl 2-[(ethoxycarbonyl)amino]-1-cyclohexene-1-carboxylate as a white solid.

Part B

Using the method of Example 1 Part B, ethyl 2-[(ethoxycarbonyl)amino]-1-cyclohexene-1-carboxylate (158 g, 0.66 mole) was reacted with sodium methoxide to provide 79 g of methyl 2-amino-1-cyclohexene-1-carboxylate as a white solid.

Part C

Using the method of Example 1 Part C, a mixture of the ethyl and methyl esters of 2-amino-1-cyclohexene-1-carboxylic acid (5 g) was reacted with methyl malonyl chloride to provide 6.3 g of a mixture of methyl 3-oxo-3-[(2-ethoxycarbonylcyclohexen-1-yl)amino]propanoate and methyl 3-oxo-3-[(2-methoxycarbonylcyclohexen-1-yl)amino]propanoate as a clear oil.

Part D

Using the general method of Example 1 Part D, a mixture of methyl 3-oxo-3-[(2-ethoxycarbonylcyclohexen-1-yl)amino]propanoate and methyl 3-oxo-3-[(2-methoxycarbonylcyclohexen-1-yl)amino]propanoate (43.2 g, 0.16 mole) was cyclized to provide 35.5 g of methyl 1,2,5,6,7,8-hexahydro-4-hydroxy-2-oxoquinoline-3-carboxylate as an off white solid.

Part E

Using the general method of Example 1 Part E, a mixture of methyl 1,2,5,6,7,8-hexahydro-4-hydroxy-2-oxoquinoline-3-carboxylate and 1,2,5,6,7,8-hexahydro-4-hydroxy-2-oxoquinoline-3-carboxylic acid (1.92 g total) was hydrolyzed and decarboxylated to provide 1.38 g of 5,6,7,8-tetrahydro-4-hydroxy-2(1H)-quinolinone as a white solid, m.p. >300° C.

Part F

Using the general method of Example 1 Part F, 5,6,7,8-tetrahydro-4-hydroxy-2(1H)-quinolinone (1.0 g, 6 mmole) was nitrated to provide 0.85 g of 5,6,7,8-tetrahydro-4-hydroxy-3-nitro-2(1H)-quinolinone as a yellow solid, m.p. 240°–244° C. (dec).

Part G

Using the general method of Example 1 Part G, 5,6,7,8-tetrahydro-4-hydroxy-3-nitro-2(1H)-quinolinone (0.50 g, 2.4 mmole) was first reacted with trifluoromethanesulfonic anhydride then with isobutylamine to provide 0.73 g of [4-(2-methylpropyl)amino-3-nitro-5,6,7,8-tetrahydroquinolin-2-yl] trifluoromethanesulfonate as a yellow oil. Analysis: Calculated for $C_{14}H_{18}F_3N_3O_5S$: %C, 42.32; %H, 4.57; %N, 10.57; Found: %C, 41.87; %H, 4.37; %N, 10.34.

EXAMPLE 5

5,6,7,8-Tetrahydro-3-nitro-2,4-bis[(trifluoromethyl)sulfonyloxy]quinoline

Trifluoromethanesulfonic anhydride (8.0 mL, 47 Mole) was added via a syringe to a cooled (0° C.) homogeneous mixture containing 5,6,7,8-tetrahydro-4-hydroxy-3-nitro-2(1H)-quinolinone (4.0 g, 19 mmole) and triethylamine (6.6 mL, 47 mmole) in methylene chloride (200 mL). The reaction mixture was stirred at 0° C. for 30 minutes. The reaction mixture was filtered through a layer of silica gel and the gel eluted with methylene chloride. The organic phase was evaporated under vacuum to provide 8.4 g of the desired product as a yellow oil.

EXAMPLE 6

5,6,7,8-Tetrahydro-4-[(2-hydroxy-2-methylpropyl)amino]-3-nitroquinolin-2-yl Trifluoromethanesulfonate Triethylamine (1.36 mL, 9.8 mmole) was added to a solution of 5,6,7,8-tetrahydro-3-nitro-2,4-bis[(trifluoromethyl)sulfonyloxy]quinoline (4.2 g, 9.4 mmole) in methylene chloride (180 mL). 2-Amino-α,α-dimethylethanol (0.88 g, 9.8 mmole) was added to the reaction mixture which was then stirred at ambient temperature overnight. The reaction mixture was evaporated to provide a residue which was purified by silica gel chromatography eluting with hexane: ethyl acetate 40:60 to provide 3.8 g of the desired product.

EXAMPLES 7–15

Using the general method of Example 6, 5,6,7,8-tetrahydro-3-nitro-2,4-bis[(trifluoromethyl)-sulfonyloxy] quinoline was reacted with an amine of formula $R_1NH_2$ to provide the intermediates of Formula X (n=2) shown in Table 1.

TABLE 1

| Example Number | Intermediate of Formula X<br>n = 2, $R_1$ = |
|---|---|
| 7 | phenylmethyl |
| 8 | n-butyl |
| 9 | 1,1-dimethylethyl |
| 10 | 1-methylpropyl |
| 11 | cyclohexylmethyl |
| 12 | 2-phenylethyl |
| 13 | cyclohexyl |
| 14 | phenyl |
| 15 | 3-hydroxypropyl |

EXAMPLE 16

5,6,7,8-Tetrahydro-$N^4$-(2-methylpropyl)-3-nitro-$N^2$, $N^2$-bis(phenylmethyl)quinoline-2,4-diamine 5,7,6,8-tetrahydro-4-[(2-methylpropyl)amino]-3-nitroquinolin-2-yl trifluoromethanesulfonate (4.0 g, 0.01 mole), dibenzylamine (1.9 mL, 0.01 mole), triethylamine (1.4 mL, 0.01 mole) and benzene (100 mL) were combined and heated at reflux for 36 hours. The benzene was evaporated under vacuum and the residue purified by silica gel chromatography eluting with hexane:ethyl acetate 70:30 to provide 4.1 g of the desired product as a viscous orange oil.

EXAMPLES 17–29

Using the general method of Example 16, intermediates of Formula X were reacted with dibenzylamine to provide the intermediates of Formula XI shown in Table 2.

TABLE 2

| Example Number | Intermediate of Formula X<br>Example | Intermediate of Formula XI<br>n = | $R_1$ = |
|---|---|---|---|
| 17 | 1 | 1 | 2-methylpropyl |
| 18 | 2 | 3 | 2-methylpropyl |
| 19 | 3 | 3 | 2-hydroxy-2-methylpropyl |
| 20 | 6 | 2 | 2-hydroxy-2-methylpropyl |
| 21 | 7 | 2 | phenylmethyl |
| 22 | 8 | 2 | n-butyl |
| 23 | 9 | 2 | 1,1-dimethylethyl |
| 24 | 10 | 2 | 1-methylpropyl |
| 25 | 11 | 2 | cyclohexylmethyl |
| 26 | 12 | 2 | 2-phenylethyl |

TABLE 2-continued

| Example Number | Intermediate of Formula X Example | Intermediate of Formula XI | |
|---|---|---|---|
| | | n = | $R_1$ = |
| 27 | 13 | 2 | cyclohexyl |
| 28 | 14 | 2 | phenyl |
| 29 | 15 | 2 | 3-hydroxypropyl |

EXAMPLE 30

$N^2,N^2,N^4$-Tris(phenylmethyl)-5,6,7,8-tetrahydroquinolin-2,3,4-triamine

Sodium borohydride (0.82 g, 22 mmole) was added to a solution of nickel(II) chloride hydrate (1.43 g, 6 mmole) in methanol (300 mL). The addition caused a black solid to form along with gas evolution. The resulting heterogeneous mixture was stirred at ambient temperature for about 30 minutes. A solution containing $N^2,N^2,N^4$-Tris(phenylmethyl)-5,6,7,8-tetrahydro-3-nitroquinolin-2,4-diamine (5.73 g, 12 mmole) in methylene chloride (20 mL) was added followed by 5 successive additions of sodium borohydride (0.38 g, 10 mmole each addition). The reaction mixture was stirred at ambient temperature for about 15 minutes then filtered through a layer of silica gel. The filtrate was evaporated. The residue was taken up in a minimum amount of methylene chloride then placed on a layer of silica gel. The silica gel was eluted with hexane:ethyl acetate 80:20. The organic phase was collected then evaporated to provide 5.0 g of the desired product as a green oil.

EXAMPLE 31–43

Using the general method of Example 30, intermediates of Formula XI were reduced to provide the intermediates of Formula XII shown in Table 3.

TABLE 3

| Example Number | Intermediate of Formula XI Example | Intermediate of Formula XII | |
|---|---|---|---|
| | | n = | $R_1$ = |
| 31 | 16 | 2 | 2-methylpropyl |
| 32 | 17 | 1 | 2-methylpropyl |
| 33 | 18 | 3 | 2-methylpropyl |
| 34 | 19 | 3 | 2-hydroxy-2-methylpropyl |
| 35 | 20 | 2 | 2-hydroxy-2-methylpropyl |
| 36 | 22 | 2 | n-butyl |
| 37 | 23 | 2 | 1,1-dimethylethyl |
| 38 | 24 | 2 | 1-methylpropyl |
| 39 | 25 | 2 | cyclohexylmethyl |
| 40 | 26 | 2 | 2-phenylethyl |
| 41 | 27 | 2 | cyclohexyl |
| 42 | 28 | 2 | phenyl |
| 43 | 29 | 2 | 3-hydroxypropyl |

Example 44

N,N-Bis(phenylmethyl)-6,7,8,9-tetrahydro-2-methyl-1-(2-methylpropyl)-1H-imidazo[4,5-c]quinolin-4-amine $N^2,N^2$-Bis(phenylmethyl)-5,6,7,8-tetrahydro-$N^4$-(2-methylpropyl)quinolin-2,3,4-triamine (1.2 g, 3 mmole) was dissolved in glacial acetic acid (5 mL) and heated at reflux for 72 hours. The reaction mixture was cooled, diluted with water (20 mL), made basic with 2N sodium hydroxide then extracted with ethyl acetate (3×50 mL). The extracts were combined, dried over magnesium sulfate then evaporated to provide 1.2 g of a yellow/green foam. This material was purified by silica gel chromatography eluting with hexane-:ethyl acetate 70:30 to provide 0.83 g of the desired product as a yellow foam.

EXAMPLES 45–64

Using the general method of Example 44, the intermediates of Formula XIII shown in Table 4 were prepared by reacting the indicated intermediate of Formula XII with the indicated ortho ester or carboxylic acid.

TABLE 4

| Example Number | Intermediate of Formula XII | Ortho ester; Carboxylic Acid | Intermediate of Formula XIII | | |
|---|---|---|---|---|---|
| | | | n | $R_1$ | $R_2$ |
| 45 | 32 | acetic acid | 1 | 2-methylpropyl | methyl |
| 46 | 34 | formic acid | 3 | 2-hydroxy-2-methylpropyl | H |
| 47 | 33 | formic acid | 3 | 2-methylpropyl | H |
| 48 | 35 | formic acid | 2 | 2-hydroxy-2-methylpropyl | H |
| 49 | 31 | methoxyacetic acid | 2 | 2-methylpropyl | methoxymethyl |
| 50 | 31 | formic acid | 2 | 2-methylpropyl | H |
| 51 | 43 | formic acid | 2 | 3-hydroxypropyl | H |
| 52 | 42 | formic acid | 2 | phenyl | H |
| 53 | 41 | formic acid | 2 | cyclohexyl | H |
| 54 | 40 | formic acid | 2 | 2-phenylethyl | H |
| 55 | 39 | formic acid | 2 | cyclohexylmethyl | H |
| 56 | 38 | formic acid | 2 | 1-methylpropyl | H |
| 57 | 36 | formic acid | 2 | n-butyl | H |
| 58 | 30 | formic acid | 2 | phenylmethyl | H |
| 59 | 32 | formic acid | 1 | 2-methylpropyl | H |
| 60 | 33 | triethyl orthoacetate | 3 | 2-methylpropyl | methyl |
| 61 | 34 | triethyl orthoacetate | 2 | 2-hydroxy-2-methylpropyl | methyl |
| 62 | 35 | triethyl orthoacetate | 2 | 2-hydroxy-2-methylpropyl | methyl |

TABLE 4-continued

| Example Number | Intermediate of Formula XII | Ortho ester; Carboxylic Acid | Intermediate of Formula XIII | | |
|---|---|---|---|---|---|
| | | | n | R₁ | R₂ |
| 63 | 31 | propionic acid | 2 | 2-methylpropyl | ethyl |
| 64 | 37 | triethyl orthoformate | 2 | 1,1-dimethylethyl | H |

EXAMPLE 65

N,N-Bis(phenylmethyl)-6,7,8,9-tetrahydro-1,2-di(2-methylpropyl)-1H-imidazo[4,5-c]quinolin-4-amine A solution containing $N^2,N^2$-bis(phenylmethyl)5,6,7,8-tetrahydro-$N^4$-(2-methylpropyl)quinolin-2,3,4-triamine (2.0 g, 4.8 mmoles) and isovaleryl chloride (0.585 mL, 4.8 mmole) in acetonitrile (50 mL) was stirred at ambient temperature for about 15 minutes. p-Toluenesulfonic acid (0.1 g) was added and the reaction mixture was heated at reflux for about 24 hours. The reaction mixture was cooled to ambient temperature and concentrated under vacuum to provide a residue which was partitioned between methylene chloride and 10% ammonium hydroxide. The organic phase was dried over magnesium sulfate and concentrated to provide 0.71 g of a yellow oil. The oil was purified by silica gel chromatography eluting with hexane:ethyl acetate 70:30 to provide 1.6 g of the desired product as a yellow foam.

EXAMPLE 66

N,N-Bis(phenylmethyl)-6,7,8,9-tetrahydro-2-(1-methylethyl)-1-(2-methylpropyl)-1H-imidazo[4,5-c]quinolin-4-amine Using the general method of Example 65, $N^2,N^2$-bis(phenylmethyl)-5,6,7,8-tetrahydro-$N^4$-(2-methylpropyl)quinolin-2,3,4-triamine (0.86 g, 2.1 mmole) was reacted with isobutyryl chloride (0.217 mL, 2.1 mmole) to provide 0.67 g of the desired product as a yellow foam.

EXAMPLE 67

N,N-Bis(phenylmethyl)-2-ethoxymethyl-6,7,8,9-tetrahydro-1-(2-hydroxy-2-methylpropyl)-1H-imidazo[4,5-c]quinolin-4-amine Using the general method of Example 65, $N^2,N^2$-bis(phenylmethyl)-5,6,7,8-tetrahydro-$N^4$-(2-hydroxy-2-methylpropyl)quinolin-2,3,4-triamine (2.1 g, 4.8 mmole) was reacted with ethoxyacetyl chloride to provide 0.8 g of the desired product.

EXAMPLE 68

N,N,2-Tris(phenylmethyl)-6,7,8,9-tetrahydro-1-(2-methylpropyl)-1H-imidazo[4,5-c]quinolin-4-amine Using the general method of Example 65, $N^2,N^2$-bis(phenylmethyl)-5,6,7,8-tetrahydro-$N^4$-(2-methylpropyl)quinolin-2,3,4-triamine (1.97 g, 4.8 mmole) was reacted with phenylacetyl chloride (527 μL, 5.2 mmole) to provide 1.3 g of the desired product as a yellow foam.

EXAMPLE 69

6,7,8,9-Tetrahydro-1,2-di(2-methylpropyl)-1H-imidazo[4,5-c]quinolin-4-amine

N,N-Bis(phenylmethyl)-6,7,8,9-tetrahydro-1,2-di(2-methylpropyl)-1H-imidazo[4,5-c]quinolin-4-amine (1.61 g, 3.3 mmole), palladium hydroxide on carbon (0.50 g, Pearlman's catalyst) and formic acid (10 mL) were combined and heated at reflux for 20 hours. The reaction mixture was cooled to ambient temperature, filtered through a layer of celite and diluted with water (about 20 mL). The resulting mixture was cooled to 0° C., made basic by the addition of 28% ammonium hydroxide then extracted with methylene chloride (3×50 mL). The extracts were combined, dried over magnesium sulfate and concentrated to provide a white solid. The solid was purified by silica gel chromatography eluting with methylene chloride:methanol 90:10 to provide 0.65 g of the desired product as a white solid, m.p.160°–161° C. Analysis: Calculated for $C_{18}H_{28}N_4$: %C, 71.96; %H, 9.39; %N, 18.65; Found: %C, 71.66; %H, 9.37; %N, 18.46.

EXAMPLE 70

6,7,8,9-Tetrahydro-2-methyl-1-(2-methylpropyl)-1H-imidazo[4,5-c]quinolin-4-amine N,N-Bis(phenylmethyl)-6,7,8,9-tetrahydro-2-methyl-1-(2-methylpropyl)-1H-imidazo[4,5-c]quinolin-4-amine (820 mg, 1.87 mmole), palladium hydroxide on carbon (200 mg, Pearlman's catalyst), ammonium formate (472 mg, 7.48 mmole) and methanol (50 mL) were combined and heated at reflux for 48 hours. During the course of the reaction additional catalyst (200 mg) and ammonium formate (472 mg) were added. The reaction mixture was cooled to ambient temperature then filtered through a layer of celite. The filtrate was evaporated to provide a residue which was dissolved in 3N hydrochloric acid. The solution was made basic (pH 9) with ammonium hydroxide then extracted with methylene chloride (3×200 mL). The extracts were combined, washed with water, dried over magnesium sulfate then concentrated to provide 480 mg of a white solid. This solid was recrystallized from ethyl acetate to provide 260 mg of the desired product as a white solid, m.p. 170°–172° C. Analysis: Calculated for $C_{15}H_{22}N_4 + \frac{1}{3}H_2O$: %C, 68.16; %H, 8.64; %N, 21.2; Found: %C, 68.47; %H, 8.14; %N, 21.08.

EXAMPLES 71–92

Using the general method of Examples 69 and 70, the products of Formula I shown in Table 5 were prepared by hydrogenolizing the indicated intermediate of Formula XIII. The melting points and elemental analyses are shown in Table 6.

TABLE 5

| Example Number | Intermediate of Formula XIII | n | R$_1$ | R$_2$ |
|---|---|---|---|---|
| 71 | 45 | 1 | 2-methylpropyl | methyl |
| 72 | 46 | 3 | 2-hydroxy-2-methylpropyl | H |
| 73 | 47 | 3 | 2-methylpropyl | H |
| 74 | 48 | 2 | 2-hydroxy-2-methylpropyl | H |
| 75 | 49 | 2 | 2-methylpropyl | methoxymethyl |
| 76 | 50 | 2 | 2-methylpropyl | H |
| 77 | 51 | 2 | 3-hydroxypropyl | H |
| 78 | 52 | 2 | phenyl | H |
| 79 | 53 | 2 | cyclohexyl | H |
| 80 | 54 | 2 | 2-phenylethyl | H |
| 81 | 55 | 2 | cyclohexylmethyl | H |
| 82 | 56 | 2 | 1-methylpropyl | H |
| 83 | 57 | 2 | n-butyl | H |
| 84 | 59 | 1 | 2-methylpropyl | H |
| 85 | 60 | 3 | 2-methylpropyl | methyl |
| 86 | 61 | 3 | 2-hydroxy-2-methylpropyl | methyl |
| 87 | 62 | 2 | 2-hydroxy-2-methylpropyl | methyl |
| 88 | 63 | 2 | 2-methylpropyl | ethyl |
| 89 | 64 | 2 | 1,1-dimethylethyl | H |
| 90 | 66 | 2 | 2-methylpropyl | 1-methylethyl |
| 91 | 67 | 2 | 2-hydroxy-2-methylpropyl | ethoxymethyl |
| 92 | 68 | 2 | 2-methylpropyl | phenylmethyl |

TABLE 6

| Example Number | m.p. (°C.) | Formula | Calculated %C | %H | %N | Found %C | %H | %N |
|---|---|---|---|---|---|---|---|---|
| 71 | 181–183 | $C_{14}H_{20}N_4 + ¼H_2O$ | 67.57 | 8.30 | 22.51 | 67.90 | 8.16 | 22.54 |
| 72 | 235–237 | $C_{15}H_{22}N_4O + ⅔CH_2Cl_2$ | 56.85 | 7.11 | 16.93 | 56.22 | 7.09 | 17.29 |
| 73 | 201–203 | $C_{15}H_{22}N_4 + ½H_2O$ | 67.38 | 8.67 | 20.95 | 67.65 | 8.34 | 20.83 |
| 74 | 247–251 | $C_{14}H_{20}N_4O$ | 64.59 | 7.74 | 21.52 | 64.10 | 7.39 | 21.22 |
| 75 | 225–230 | $C_{16}H_{24}N_4O + ½CH_2Cl_2 + ½H_2O$ | 58.48 | 7.45 | 16.53 | 57.87 | 7.47 | 16.84 |
| 76 | 223–225 | $C_{14}H_{20}N_4$ | 68.82 | 8.25 | 22.93 | 69.16 | 8.24 | 22.65 |
| 77 | 232–234 | $C_{13}H_{18}N_4O + ⅓H_2O$ | 61.91 | 7.43 | 22.22 | 62.43 | 7.20 | 22.38 |
| 78 | >300 | $C_{16}H_{16}N_4 + ⅔CH_2Cl_2$ | 62.37 | 5.44 | 17.45 | 61.86 | 5.17 | 17.85 |
| 79 | 238–241 | $C_{16}H_{22}N_4 + ⅓H_2O$ | 70.14 | 8.24 | 20.45 | 70.58 | 8.14 | 20.45 |
| 80 | 209–211 | $C_{18}H_{20}N_4 + ½H_2O$ | 71.73 | 7.02 | 18.59 | 71.69 | 6.75 | 18.63 |
| 81 | 210–212 | $C_{17}H_{24}N_4 + ⅓H_2O$ | 70.46 | 8.56 | 19.33 | 70.26 | 8.30 | 19.42 |
| 82 | 182–185 | $C_{14}H_{20}N_4 + H_2O$ | 67.31 | 8.34 | 22.43 | 67.33 | 8.05 | 22.34 |
| 83 | 196–198 | $C_{14}H_{20}N_4 + ¼H_2O$ | 67.57 | 8.30 | 22.51 | 67.89 | 8.13 | 22.63 |
| 84 | 204–206 | $C_{13}H_{18}N_4$ | 67.80 | 7.88 | 24.33 | 67.44 | 7.85 | 24.09 |
| 85 | 179–182 | $C_{16}H_{24}N_4$ | 70.55 | 8.88 | 20.57 | 70.17 | 8.96 | 20.35 |
| 86 | 275–277 | $C_{16}H_{24}N_4O + ¼CH_2Cl_2$ | 63.04 | 7.98 | 18.09 | 63.37 | 8.06 | 18.29 |
| 87 | 287–290 | $C_{15}H_{22}N_4 + H_2O$ | 61.62 | 8.27 | 19.16 | 61.94 | 7.60 | 18.82 |
| 88 | 156–159 | $C_{16}H_{24}N_4 + ½H_2O$ | 68.29 | 8.95 | 19.91 | 67.90 | 8.36 | 19.53 |
| 89 | 225–227 | $C_{14}H_{20}N_4 + ¼ H_2O$ | 67.57 | 8.30 | 22.51 | 67.77 | 8.06 | 22.09 |
| 90 | 151–153 | $C_{17}H_{26}N_4 + ⅓H_2O$ | 69.84 | 9.19 | 19.16 | 70.01 | 9.11 | 18.69 |
| 91 | 165–167 | $C_{17}H_{26}N_4O_2 + ½H_2O$ | 62.95 | 8.29 | 17.27 | 62.96 | 8.06 | 16.90 |
| 92 | 155–156 | $C_{21}H_{26}N_4 + H_2O$ | 71.56 | 8.01 | 15.89 | 71.20 | 7.54 | 15.79 |

EXAMPLE 93

N,N-Bis(phenylmethyl)-6,7,8,9-tetrahydro-1-(2-methylpropyl)-2-phenylmethoxymethyl-1H-imidazo[4,5-c]quinolin-4-amine Using the general method of Example 65, $N^2,N^2$-bis(phenylmethyl)-5,6,7,8-tetrahydro-$N^4$-(2-methylpropyl)quinolin-2,3,4-triamine (2.3 g, 5.5 mmole) was reacted with benzyloxyacetyl chloride (1.0 g, 5.5 mmoles) to provide 2.0 g of the desired product as a clear oil.

EXAMPLE 94

4-Amino-6,7,8,9-tetrahydro-1-(2-methylpropyl)-1H-imidazo[4,5-c]quinolin-2-methanol Using the general method of Example 69, N,N-bis(phenylmethyl)-6,7,8,9-tetrahydro-1-(2-methylpropyl)-2-phenylmethoxymethyl-1H-imidazo[4,5-c]quinolin-4-amine (2.0 g, 3.7 mmole) was hydrogenolized to provide 0.71 g of the desired product as an off-white solid, m.p. 226°–226° C. Analysis: Calculated for $C_{15}H_{22}N_4O+¼H_2O$: %C, 64.61; %H, 8.13; %N, 20.09; Found: %C, 64.67; %H, 7.88; %N, 20.03.

EXAMPLE 95

6,7,8,9-Tetrahydro-1-(2-methylpropyl)-2-morpholinomethyl-1H-imidazo[4,5-c]quinolin-4-amine 4-Amino-6,7,8,9-tetrahydro-1-(2-methylpropyl)-1H-imidazo[4,5-c]quinolin-2-methanol (100 mg, 0.365 mmole)

was slowly added to thionyl chloride (1 mL). The resulting mixture was stirred at ambient temperature for 3 hours. The thionyl chloride was removed under vacuum. The resulting residue was diluted with methylene chloride (5 mL), combined with morpholine (1 mL) and heated at reflux for 10 hours. The reaction mixture was cooled to ambient temperature, quenched with saturated sodium bicarbonate solution and then extracted with methylene chloride (3×20 mL). The extracts were combined, dried over magnesium sulfate and concentrated to provide a greenish oil. The oil was purified by silica gel chromatography eluting with methylene chloride:methanol 90:10 to provide 72 mg of the desired product as a light green solid, m.p. 165°–172° C. Analysis: Calculated for $C_{19}H_{29}N_5O+\frac{1}{3}H_2O$: %C, 65.24; %H, 8.54; %N, 20.11; Found: %C, 65.71; %H, 8.43; %N, 19.77.

EXAMPLE 96

6,7,8,9-Tetrahydro-1-phenylmethyl-1H-imidazo[4,5-c]quinolin-4-amine

N,N,1-Tris(phenylmethyl)-6,7,8,9-tetrahydro-1H-imidazo[4,5-c]quinolin-4-amine (4.49 g, 9.8 mmole), palladium hydroxide on carbon (1.0 g, Pearlman's catalyst) and formic acid (20 mL) were combined and heated at reflux for 4 days. During the course of the reaction the formic acid evaporated out of the reaction vessel. The residue was diluted with formic acid (15 mL) and water (20 mL) then filtered through a layer of celite. The filtrate was basified with 28% ammonium hydroxide then extracted with methylene chloride (3×100 mL). The methylene chloride extracts were combined, dried over magnesium sulfate and concentrated to provide 2.5 g of a yellow foam. The foam was loaded onto a 3 cm by 15 cm column of silica gel and eluted with methylene chloride:methanol 90:10. The early fractions were combined and evaporated to provide 0.54 g of N,2-bis(phenylmethyl)-6,7,8,9-tetrahydro-1H-imidazo[4,5-c]quinolin-4-amine as an off-white solid, m.p. 199°–200° C. The later fractions were combined and evaporated to provide 1.58 g of a mixture of 6,7,8,9-tetrahydro-N-phenylmethyl-1H-imidazo[4,5-c]quinolin-4-amine and 6,7,8,9-tetrahydro-1-phenylmethyl-1H-imidazo[4,5-c]quinolin-4-amine as an off-white solid. This mixture was loaded onto a 3 cm by 20 cm column of silica gel and eluted with methylene chloride:methanol 90:10. 80 fractions, 6 mL each, were collected. Fractions 18–27 were combined and evaporated to provide 0.48 g of 6,7,8,9-tetrahydro-N-phenylmethyl-1H-imidazo[4,5-c]quinolin-4-amine as a white solid, m.p. 168°–170° C. Fractions 40–57 were combined and evaporated to provide 180 mg of the desired product, 6,7,8,9-tetrahydro-1-phenylmethyl-1H-imidazo[4,5-c]quinolin-4-amine, as a white solid, m.p. 231°–233° C. (dec). Analysis: Calculated for: $C_{18}H_{19}N_4+\frac{1}{5} CH_2Cl_2$: %C, 69.95; %H, 6.28; %N, 18.97; Found: %C, 70.44; %H, 6.16; %N, 18.93.

EXAMPLE 97

6,7,8,9-Tetrahydro-1H-imidazo[4,5-c]quinolin-4-amine

Using the method of Example 70, 6,7,8,9-tetrahydro-N-phenylmethyl-1H-imidazo[4,5-c]quinolin-4-amine (200 mg, Example 96) was hydrogenolized to provide 66 mg of the desired product as a solid, m.p. >300° C. Analysis: Calculated for $C_{10}H_{12}N_4+\frac{1}{3}H_2O$: %C, 61.85; %H, 6.58; %N, 28.85; Found: %C, 62.09; %H, 6.33; %N, 28.79.

EXAMPLE 98

1-(3-Chloropropyl)-6,7,8,9-tetrahydro-1H-imidazo[4,5-c]quinolin-4-amine

Dimethylformamide was added dropwise to 4-amino-6,7,8,9-tetrahydro-1H-imidazo[4,5-c]quinoline-1-propanol (1.06 g) until a solution was obtained. Thionyl chloride (0.63 mL) was added and the reaction mixture was heated for 45 minutes before being evaporated to dryness. The residue was taken up in ice water then made basic with saturated sodium bicarbonate solution. The resulting precipitate was collected and dried to provide 0.32 g of a dark brown solid. This material was purified by silica gel column chromatography eluting with 85:15 methylene chloride:methanol to provide 0.28 g of the desired product as a solid m.p. 245°–247° C. Analysis: Calculated for $C_{13}ClH_{17}N_4+1.5 H_2O$: %C, 53.51; %H, 6.91; %N, 19.2; Found: %C, 53.81; %H, 6.25; %N, 18.86.

INTERFERON (α) INDUCTION IN HUMAN CELLS

The test method described below demonstrates the ability of compounds of the invention to induce the biosynthesis of interferon (α) in human cells.

An in vitro human blood cell system was used to assess interferon induction by compounds of the invention. Activity is based on the measurement of interferon secreted into culture media. Interferon is measured by bioassay.

Blood Cell Preparation for Culture

Whole blood is collected by venipuncture into EDTA vacutainer tubes. Peripheral blood mononuclear cells (PBM's) are separated from whole blood by using either LeucoPREP™ Brand Cell Separation Tubes (available from Becton Dickinson) or Ficoll-Paque® solution (available from Pharmacia LKB Biotechnology Inc, Piscataway, N.J.). The PBM's are suspended at 1×10⁶/mL in RPMI 1640 media (available from GIBCO, Grand Island, N.Y.) containing 25 mM HEPES (N-2-hydroxyethylpiperazine-N'-2-ethanesulfonic acid) and L-glutamine (1% penicillin-streptomycin solution added) with 10% heat inactivated (56° C. for 30 minutes) autologous serum added. 200 µL portions of PBM suspension are added to 96 well (flat bottom) MicroTest III sterile tissue culture plates.

Compound Preparation

The compounds are solubilized in ethanol, dimethyl sulfoxide or tissue culture water then diluted with tissue culture water, 0.01N sodium hydroxide or 0.01N hydrochloric acid (The choice of solvent will depend on the chemical characteristics of the compound being tested.). Ethanol or DMSO concentration should not exceed a final concentration of 1% for addition to the culture wells. Compounds are initially tested in a concentration range of from about 0.1 µg/mL to about 5 µg/mL. Compounds which show induction at a concentration of 0.5 µg/mL are then tested in a wider concentration range.

Incubation

The solution of test compound is added in a volume (less than or equal to 50 µL) to the wells containing 200 µL of diluted whole blood or of PBM's in media. Solvent and/or media is added to control wells (wells with no test compound) and as needed to adjust the final volume of each well to 250 µL. The plates are covered with plastic lids, vortexed gently and then incubated for 48 hours at 37° C. with a 5% carbon dioxide atmosphere.

Separation

Following incubation, the plates are covered with parafilm and then centrifuged at 1000 rpm for 10 to 15 minutes at 4° C. in a Damon IEC Model CRU-5000 centrifuge. Media (about 200 µL) is removed from 4 to 8 wells and pooled into 2 mL sterile freezing vials. Samples are maintained at −70° C. until analysis.

Interferon Analysis/Calculation

Interferon is determined by bioassay using A549 human lung carcinoma cells challenged with encephalomyocarditis.

The details of the bioassay method have been described by G. L. Brennan and L. H. Kronenberg in "Automated Bioassay of Interferons in Micro-test Plates", Biotechniques, June/July, 78, 1983, incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantifying for vital cytopathic effect. The viral cytopathic effect is quantified by staining followed by spectrophotometric absorbance measurements. Results are expressed as alpha reference units/mL based on the value obtained for NIH HU IF-L standard. The interferon was identified as essentially all interferon alpha by testing in checkerboard neutralization assays against rabbit anti-human interferon (beta) and goat anti-human interferon (alpha) using A549 cell monolayers challenged with encephalomyocarditis virus. Results are shown in the table below wherein the absence of an entry indicates that the compound was not tested at that particular concentration.

| Interferon (α) Induction in Human Cells | | | | | | |
|---|---|---|---|---|---|---|
| Compound of Example | α Reference Units/mL Dose Concentration (µg/mL) | | | | | |
| Number | 0.01 | 0.05 | 0.10 | 0.50 | 1.0 | 5.0 |
| 69 | 2 | 59 | 340 | 260 | 310 | 700 |
| 70 | 6 | 6 | 40 | 110 | 190 | 120 |
| 71 | 6 | 6 | 130 | 270 | 320 | 370 |
| 72 | | | 2 | 48 | 2800 | 2500 |
| 73 | 4 | 4 | 4 | 22 | 67 | 130 |
| 74 | | | 2 | 2 | 21 | 1300 |
| 75 | 4 | 4 | 38 | 82 | 96 | 200 |
| 76 | 6 | 6 | 6 | 6 | 38 | 97 |
| 77 | 1 | 1 | 1 | 1 | 480 | 430 |
| 78 | 1 | 1 | 1 | 1 | 37 | 15 |
| 79 | 2 | 1 | 2 | 1 | 1 | 1 |
| 80 | 1 | 140 | 170 | 15 | 13 | 13 |
| 81 | 1 | 1 | 1 | 13 | 15 | 1 |
| 82 | 2 | 2 | 2 | 320 | 400 | 130 |
| 83 | 7 | 26 | 74 | 930 | 410 | 130 |
| 84 | | | 6 | 6 | 6 | 13 |
| 85 | 4 | 4 | 77 | 82 | 110 | 150 |
| 86 | 4 | 4 | 17 | 220 | 130 | 210 |
| 87 | 3 | 360 | 1100 | 280 | 140 | 260 |
| 88 | 6 | 75 | 210 | 260 | 260 | 290 |
| 89 | 2 | 2 | 2 | 2 | 2 | 2 |
| 90 | 2 | 2 | 2 | 2 | 4 | 670 |
| 91 | 290 | 330 | 210 | 290 | 290 | 290 |
| 92 | 0 | 170 | 170 | 66 | 88 | 130 |
| 94 | 2 | 140 | 880 | 170 | 170 | 170 |
| 95 | 2 | 2 | 2 | 590 | 660 | 260 |
| 96 | | | 2 | 1200 | 850 | 280 |
| 97 | 3 | 3 | 3 | 45 | 740 | 410 |

INDIRECT IN-VITRO ANTIVIRAL ACTIVITY

The test method described below demonstrates the ability of compounds of the invention to inhibit the progress of vital infection.

Whole blood is collected by venipuncture into EDTA vacutainer tubes. Peripheral blood mononuclear cells (PBM's) are isolated using Ficoll-Paque® solution (available from Pharmacia LKB Biotechnology Inc., Piscataway, N.J.). The PBM's are washed with phosphate buffer saline then diluted with RPMI 1640 medium (available from GIBCO, Grand Island, N.Y.) and 10% fetal bovine serum to obtain a final concentration of 2.5×10⁶ cells/mL. One mL portions of PBM's in medium are placed in 15 mL polypropylene tubes. The test compound is dissolved in dimethyl sulfoxide then diluted with RPMI 1640 medium. The solution of test compound is added to the tubes containing the PBM's to give final concentrations ranging from 0.01 µg/mL to 1.0 µg/mL. Control tubes do not receive any test compound. The tubes are then incubated for 24 hours at 37° C. with a 5% carbon dioxide atmosphere. Following incubation the tubes are centrifuged at 400× g for 5 minutes. The supernatant is removed. The PBM's are brought up in 100 µL of RPMI 1640 medium and then infected with a 100 µL containing $10^5$ tissue culture 50% infectious doses of vesicular stomatitis virus (VSV). The tubes are incubated for 30 minutes at 37° C. to allow virus adsorption. One mL of RPMI 1640 medium is added to each tube and the tubes are incubated for 48 hours at 37° C. The tubes are frozen then thawed to lyse the cells. The tubes are centrifuged at 400× g for 5 minutes to remove cellular debris then the supernatant is assayed by serial tenfold dilutions on Vero cells in 96 well microtiter plates. The infected cells are incubated for 24 hours at 37° C. before quantifying for viral cytopathic effect. The viral cytopathic effect is quantified by staining with 0.05% crystal violet. Results are presented as VSV inhibition, defined as the $\log_{10}$ (control VSV yield/experimental VSV yield). Control tubes have a value of 0. Results are shown in the table below wherein the absence of an entry indicates that the compound was not tested at that particular concentration.

| In-vitro Antiviral Activity | | | | | |
|---|---|---|---|---|---|
| Compound of Example | VSV Yield Inhibition Dose Concentration (µg/mL) | | | | |
| Number | 0.01 | 0.05 | 0.10 | 0.50 | 1.0 |
| 70 | 3.0 | 7.0 | 7.0 | | |
| 71 | | | 5.0 | 5.0 | 6.0 |
| 72 | | | 1.0 | 2.0 | 2.0 |
| 73 | | | 1.0 | 2.0 | 4.0 |
| 74 | | | 2.0 | 3.0 | 2.0 |
| 75 | | | 4.0 | 4.0 | 5.0 |
| 76 | | | 4.0 | 7.0 | 7.0 |
| 78 | | | 0.0 | 3.0 | 4.0 |
| 80 | | | 6.0 | 6.0 | 7.0 |
| 81 | | | 1.0 | 4.0 | 5.0 |
| 82 | | | 0.0 | 3.0 | 5.0 |
| 83 | | | 4.0 | 6.0 | 6.0 |
| 84 | | | 2.0 | 2.0 | 4.0 |
| 85 | | | 4.0 | 5.0 | 5.0 |
| 86 | | | 1.0 | 7.0 | 6.0 |
| 87 | | | 4.0 | 6.0 | 6.0 |
| 88 | 5.0 | 8.0 | | | 8.0 |
| 90 | | | | 3.0 | 8.0 |
| 92 | | | 2.0 | 4.0 | 6.0 |
| 94 | 7.0 | 8.0 | 8.0 | | |
| 96 | | | 2.0 | 4.0 | 6.0 |

We claim:

1. A compound of the formula

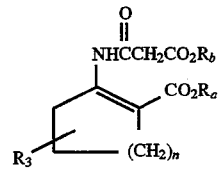

wherein n is 1, 2, or 3, $R_3$ is selected from the group consisting of hydrogen, fluoro, chloro, straight chain or branched chain alkyl containing one to about four carbon atoms, and straight chain or branched chain fluoro- or chloroalkyl containing one to about four carbon atoms and at least one fluorine or chlorine atom, $R_a$ is a group that renders the associated ester group susceptible of nucleophilic attack by an anion derived from an active methylene compound, and $R_b$ is a group that renders the associated ester group susceptible of hydrolysis.

* * * * *